US012782249B2

(12) United States Patent
Richter et al.

(10) Patent No.: US 12,782,249 B2
(45) Date of Patent: Nov. 3, 2026

(54) PNEUMATIC MODULE FOR A GAS ANALYSIS DEVICE, PRODUCTION METHOD AND COMPUTER PROGRAM PRODUCT

(71) Applicant: Siemens Aktiengesellschaft, Munich (DE)

(72) Inventors: Josef Richter, Karlsruhe (DE); Piotr Strauch, Rülzheim (DE)

(73) Assignee: Siemens Aktiengesellschaft, Munich (DE)

( * ) Notice: Subject to any disclaimer, the term of this patent is extended or adjusted under 35 U.S.C. 154(b) by 690 days.

(21) Appl. No.: 18/110,963

(22) Filed: Feb. 17, 2023

(65) Prior Publication Data

US 2023/0266207 A1 Aug. 24, 2023

(30) Foreign Application Priority Data

Feb. 21, 2022 (EP) .................................... 22157753

(51) Int. Cl.
*G01N 1/22* (2006.01)
*G01N 33/00* (2006.01)

(52) U.S. Cl.
CPC ......... *G01N 1/2247* (2013.01); *G01N 1/2273* (2013.01); *G01N 33/0016* (2013.01)

(58) Field of Classification Search
CPC ............... G01N 1/2247; G01N 1/2273; G01N 33/0016; F16K 17/20; F16K 11/00; F16K 27/00
See application file for complete search history.

(56) References Cited

U.S. PATENT DOCUMENTS

| | | | | |
|---|---|---|---|---|
| 5,010,776 A * | 4/1991 | Lucero | B09B 1/00 73/863.23 |
| 5,245,857 A * | 9/1993 | Kahl | G01N 33/0016 73/23.2 |
| 8,196,480 B1 | 6/2012 | Mayeaux | |
| 10,192,723 B2 | 1/2019 | Verenchikov et al. | |
| 2002/0180109 A1 | 12/2002 | Mussler | |

(Continued)

FOREIGN PATENT DOCUMENTS

| | | |
|---|---|---|
| CN | 112272859 | 1/2021 |
| DE | 1498517 | 5/1969 |

(Continued)

OTHER PUBLICATIONS

Bedienungsanleitung "Prozess-Gaschromatograph MicroSAM" der Siemens AG, Ausgabe Mar. 2012; 2012.

(Continued)

*Primary Examiner* — David Z Huang
(74) *Attorney, Agent, or Firm* — Cozen O'Connor

(57) ABSTRACT

A method for producing a pneumatic module, a gas analysis device comprising at least one such pneumatic module, a computer program product via which the operating characteristics of a corresponding pneumatic module can be simulated, wherein the pneumatic module serves to adjust a fluid flow and is deployable in the gas analysis device and includes a support sleeve and a flow module that is contained in the support sleeve, where the flow module is connected at a first end thereof to the support sleeve in order to achieve greater measuring accuracy of the gas analysis device.

15 Claims, 5 Drawing Sheets

(56) References Cited

U.S. PATENT DOCUMENTS

| | | | | |
|---|---|---|---|---|
| 2017/0286572 | A1* | 10/2017 | Hershey .................... | B64F 5/60 |
| 2020/0326320 | A1 | 10/2020 | Querrey et al. | |
| 2021/0265150 | A1 | 8/2021 | Arnold et al. | |

FOREIGN PATENT DOCUMENTS

| | | |
|---|---|---|
| DE | 4113695 | 10/1992 |
| DE | 19814650 | 10/1999 |
| KR | 102241270 | 4/2021 |

OTHER PUBLICATIONS

EP Search Report dated Jul. 18, 2022 based on EP22157753 filed Feb. 21, 2022.

* cited by examiner 40, 100

PNEUMATIC MODULE FOR A GAS ANALYSIS DEVICE, PRODUCTION METHOD AND COMPUTER PROGRAM PRODUCT

BACKGROUND OF THE INVENTION

1. Field of the Invention

The invention relates to a pneumatic module for a gas analysis device and to a gas analysis device which is equipped with the pneumatic module, a production method for producing the pneumatic module, and to a computer program product for simulating the operating characteristics of the pneumatic module.

2. Description of the Related Art

U.S. Pat. No. 10,192,723 B2 discloses a device for the mass-spectrometric analysis of substances, said device comprising a quartz capillary tube via which a substance sample is transported to a nozzle. A mass spectrometer is arranged adjacent to the nozzle.

U.S. Pub. No. 2002/0180109 A1 discloses a throttle that is formed from a hose blank via a securing clamp, where a mandrel is introduced into the hose blank during deformation by the securing clamp.

The operating instructions, entitled "Prozess-Gas-Chromatograph MicroSAM" published by Siemens AG, Issue March 2012, disclose a gas analysis device in which restrictors are arranged.

It is desirable in the field of gas analysis devices to achieve greater measuring accuracy and resilience against the operating conditions that are present. It is also desirable for the design of gas analysis devices to be more compact and for the production thereof to be more cost-efficient: greater ease of repair is also important.

SUMMARY OF THE INVENTION

It is an object of the invention to provide a provide methods and devices that provide an improvement in at least one of the cited aspects.

This and other objects and advantages are achieved in accordance with the invention by a pneumatic module that is configured to adjust a fluid flow in a gas analysis device. The adjustment of the fluid flow is effected by using the pneumatic module to provide a defined flow resistance, such that an absolute pressure drop occurs therein when the fluid flow is correspondingly strong. The fluid flow can be a flow of, e.g., a substance sample, a carrier gas, or a mixture thereof. The pneumatic module has a support sleeve in which a flow module is contained. During operation of the pneumatic module, the fluid flow flows through the flow module, this being configured to act on the fluid flow, for example, presenting a flow resistance to the fluid flow. In accordance with the invention, the flow module is connected at its first end, i.e., in the region of its first end, to the support sleeve. By virtue of the connection at the first end of the flow module, it is essentially surrounded completely by the support sleeve. A thin circumferential intermediate space is formed between the support sleeve and the flow module. The flow module is shielded by the support sleeve against mechanical and thermal influences from the environment. The smaller a wall thickness, an inner and/or outer diameter of the flow module, the greater its sensitivity to such influences. This can impair the effect of the flow module on the fluid flow, thereby in turn reducing the measuring accuracy that can be achieved. Mechanical influences on the flow module are obstructed by the support sleeve. The connection between the support sleeve and the flow module at the first end thereof can be formed in a compact manner, so that a contact surface that allows heat to be conducted from the support sleeve to the flow module or from the flow module to the support sleeve is minimized.

The thermal shielding of the flow module by the support sleeve is thereby ensured while at the same time a stable fixture of the flow module is provided. Among other things, a higher operating temperature of the pneumatic module is therefore possible. By virtue of the thermal shielding by the support sleeve, the connection between the support sleeve and the flow module at the first end thereof serves to increase the operating temperature of the pneumatic module. The connection between the support sleeve and the flow module at the first end thereof likewise serves to increase the measuring accuracy that can be achieved by the gas analysis device in which such a pneumatic module is deployed.

In an embodiment of the pneumatic module, the flow module is connected in a non-detachable manner at its first end to the support sleeve. A non-detachable connection is understood to be a connection that can only be detached destructively. In particular, the flow module can be connected to the support sleeve with a material bond, via a welded connection, for example, a spot-welded connection, a laser-welded connection, an electron-beam welded connection, a soldered connection, a hard-soldered connection or an adhesive connection. Such non-detachable connections can be produced automatically with a high level of precision and process reliability. Such a non-detachable connection offers greater sealing effect. The non-detachable connection can take the form of a cylindrical shell in the region of the first end. The longer this form, the greater the sealing effect that is achieved. It is moreover possible by using such connections to reduce any heat input into the flow module during production. The smaller the heat input into the flow module, the less it is distorted. The inventive pneumatic module can be manufactured automatically to a large extent, whereby the production thereof can be performed quickly, accurately and in a cost-efficient manner. This also allows the use of flow modules and/or support sleeves which are more delicate, i.e., have thinner walls. This in turn allows greater miniaturization of the pneumatic module and a gas analysis device equipped therewith. Alternatively, a detachable connection can be formed between the support sleeve and the flow module in the region of the first end. Such a detachable connection can be formed as a screw connection or bayonet connection, for example.

Furthermore, in the inventive pneumatic module, a second end of the flow module can open into an interior chamber of the support sleeve. The flow module can be essentially tubular in configuration, such that a fluid flow that enters via the first end can emerge into the interior chamber of the support sleeve at the second end. The support sleeve extends along its main axis beyond the second end of the flow module. The second end of the flow module is therefore shielded against the environment. The second end is therefore protected from direct heat inputs during production, whereby distortion due to thermal influence is prevented in the region of the second end. The flow module can therefore be delicate in the region of its second end, i.e., having reduced wall thickness, for example.

Moreover, the support sleeve in the region of the first end of the flow module can be configured for assembly into the gas analysis device. The support sleeve can also be provided with, for example, a thread, a retaining projection, a shoulder and/or a sealing device, such as an O-ring, on its exterior surface. The support sleeve can further be structured such that, in the assembled state in the gas analysis device, the fluid flow enters the pneumatic module at the first end of the flow module. The support sleeve can be configured as a standardized connection interface in the region of the first end of the flow module. It is consequently possible to deploy different flow modules in support sleeves of the same type. This allows the use of identical parts for the support sleeve when producing the inventive pneumatic module. Connection interfaces for the inventive pneumatic module can therefore be formed in a structurally identical manner in the associated gas analysis device. The production cost of the inventive pneumatic module and the corresponding gas analysis device is thereby reduced. Contact and in particular manual contact with the flow module is likewise minimized. Any penetration of foreign matter such as fats or oils that could have an interfering effect in a measurement operation of the gas analysis device is prevented. The pneumatic module can also have a maximum operating temperature, i.e., a maximum temperature of the fluid flow that flows through during operation, which essentially corresponds to a maximum operating temperature of at least one of the sealing structure. The inventive pneumatic module offers adequate thermal shielding of the flow module by virtue of the thermal dimensioning of the sealing structure for the pneumatic module. In particular, the maximum operating temperature of the pneumatic module can be up to 40° C., preferably up to 15° C., most preferably up to 10° C. lower than the maximum operating temperature of one of the sealing means.

In a further embodiment of the inventive pneumatic module, the support sleeve can comprise a single part or multiple parts. In the case of a single-part support sleeve, the number of manufacturing steps is reduced and the number of sealing points is minimized. In the case of a multi-part support sleeve, for example, a first section in which the first end of the flow module is connected to the support sleeve can be manufactured with a closer tolerance than an adjoining second section that surrounds the flow module and is essentially separated therefrom by only the thin intermediate space. Alternatively or additionally, the first and second sections of the support sleeve can be produced from different materials, thereby allowing materials to be selected according to requirements. The first or second section of the support sleeve can be produced in different ways, depending on the manufacturing tolerance that is required. This ensures greater cost efficiency when producing the claimed pneumatic module.

Moreover, the support sleeve can be formed within the inventive pneumatic module to be closed in a region of the second end of the flow module. A fluid flow emerging at the second end of the flow module is thus prevented from emerging into the environment and can be fed back through the support sleeve in the thin circumferential intermediate space to a region of the first end of the flow module. An improved sealing effect is achieved thus. The support sleeve can also be provided with an outlet opening, in particular in the region of the first end of the flow module. The outlet opening in the support sleeve can be formed as, for example, an outlet hole, such as a radial hole relative to the main axis of the support sleeve. The inventive pneumatic module can be assembled into the gas analysis device in a simple and resilient manner thus. In particular, the support sleeve that is closed in the region of the second end simplifies any automatic handling during assembly, e.g., by a robot. The inventive pneumatic module therefore allows a greater degree of automation during the production of corresponding gas analysis devices. As a result of this, further miniaturization of the inventive pneumatic module is also possible.

The support sleeve can also be configured to be closed by a cover fixed in a non-detachable manner in the region of the second end of the flow module. A non-detachable fixture here is understood to be a connection whose detachment necessarily involves destruction. The cover can be connected to the support sleeve with a material bond, for example, i.e., via a welded connection, a spot-welded connection, a laser-welded connection, an electron-beam welded connection, a soldered connection, a hard-soldered connection or an adhesive connection. Accordingly, the support sleeve can have an assembly opening along its main axis in the region of the second end of the flow module. The assembly opening is structured for insertion of the flow module and is dimensioned correspondingly. In particular, the assembly opening can be dimensioned such that the flow module can be inserted through the opening and can be held in the region of the first end of the flow module during connection of the flow module to the support sleeve. This allows production of the pneumatic module to be further automated. The cover can be connected to the support sleeve at the assembly opening in a further separate step. The cover can easily be connected to the support sleeve in a reliably impervious manner. As a result of the greater automation thus achieved, the production of the inventive pneumatic module is further accelerated. Equally, the use of more delicate flow modules is possible thus, because manual handling of the flow module is minimized in comparison with known solutions.

In a further embodiment of the inventive pneumatic module, the flow module and/or the support sleeve are produced at least partially from a metallic material. In particular, the support sleeve and the flow module can be produced from metallic materials that have advantageous properties in terms of reciprocal suitability for being connected with a material bond, for example, weldability. Metallic materials offer sufficient stability to allow automatic assembly of the pneumatic module. Moreover, the flow module and the support sleeve can be produced from materials that have a greater resistance to heat conduction when connected with a material bond. It is thereby possible further to reduce any heat input from the support sleeve into the flow module. Moreover, the flow module and/or the support sleeve can be provided with a coating that renders them inert. By virtue of that coating that renders the flow module and/or the support sleeve inert, chemical reactions between the metallic surfaces and the fluid flowing through are minimized and interfering influences in the measurement operation are reduced thus. Alternatively or additionally, the support sleeve can also be produced from a plastic material, such as a fiber composite material, which offers greater resistance to hydrogen embrittlement. The inventive pneumatic module is consequently durable for continuous operation using hydrogen or a hydrogen-containing gas mixture as a fluid.

Furthermore, the flow module can have a minimum inner diameter of 1 μm to 2 mm and/or a wall thickness of up to 5 mm. The minimum inner diameter is understood in particular to mean a minimum inner diameter in the second section of the support sleeve through which the flow module extends. Sufficiently precise production methods are readily available for such dimensions. The flow module is essentially dimensioned to achieve an aerodynamic similarity coefficient (for example, a Reynolds number or a pipe friction coefficient) that is required for the respective application scenario. It is consequently also possible to selectively act on the fluid flow using corresponding dimensions of the flow module. At the same time, the use of such compact or delicate flow modules is suitable in practice by virtue of the inventive pneumatic module, because the support sleeve offers adequate protection against influences from the environment and allows ease of handling.

In a further embodiment of the inventive pneumatic module, the flow module can be formed as a pinch throttle. The pinch throttle is essentially configured as a small tube having a cross section that is reduced in size in a central region by means of plastic deformation. The pinch throttle is configured to act as a flow resistance on the fluid flow, i.e., to bring about a defined pressure drop in the fluid flow. Pinch throttles are susceptible to thermal expansion and mechanical deformation, and therefore their effect as a flow resistance is influenced as a result of heat input or bending. The inventive pneumatic module offers greater protection against heat input from the environment, and mechanical deformation, and ensures reliable and precise operation and greater ease of maintenance of the pinch throttle. As a consequence, it is possible to adjust and reproduce the fluid flow with particular precision by means of the inventive pneumatic module. This in turn allows the gas analysis device to be operated with greater reliability and measuring accuracy. The flow module can also be formed as an aperture.

The objects and advantages are also achieved in accordance with the invention by an inventive method for producing a pneumatic module which is suitably configured for use in a gas analysis device. The gas analysis device can be configured as a gas analyzer, for example, in particular a continuous gas analyzer (CGA), or as a gas chromatograph. The method comprises a first step, in which a support sleeve and a flow module are provided for the purpose of producing the pneumatic module. The method further comprises a second step, in which the flow module is inserted into an interior chamber of the support sleeve. The insertion comprises holding the flow module in a predetermined position in which it will be fixed. During this activity, a first end of the flow module is placed directly adjacent to the support sleeve. The method further comprises a third step, in which a non-detachable connection is produced between the support sleeve and the flow module in the region of the first end of the flow module, these thereby forming the pneumatic module that is to be produced. As a result of the third step, the support sleeve and the flow module can only be detached from each other destructively. The non-detachable connection can take the form of a connection with a material bond, for example. In accordance with the inventive method, the second and/or third steps are performed automatically. For example, the flow module can be inserted into the support sleeve via a robot. Alternatively or additionally, the non-detachable connection in the third step can be produced as a welded connection by a robot. The inventive method comprises steps that can be implemented automatically in a manner that is simple and precise at the same time. This allows an accelerated production of the pneumatic modules, which can quickly be assembled into gas analysis devices and exchanged. The pneumatic modules can be tested separately with respect to their operation and tightness. Checking in the installed state in the gas analysis device is therefore unnecessary. The inventive method can readily be adapted for variously dimensioned flow modules and/or support sleeves. The inventive method consequently allows pneumatic modules to be produced with process reliability, speed and therefore cost-efficiency.

The pneumatic module that is produced using the inventive method can be configured in accordance with the disclosed embodiment of the invention. The technical advantages of the inventive pneumatic modules can therefore be transferred analogously to the inventive method. The features described in connection with the claimed pneumatic modules therefore apply to the claimed method correspondingly.

The objects and advantages in accordance with the invention are likewise achieved by an inventive gas analysis device. The gas analysis device comprises a conduction block having a plurality of channels. The plurality of channels are formed as voids in the conduction block. At least two channels are connected together via an exchangeable pneumatic module. One of the channels can be formed as a feed channel for a fluid flow, for example, and the other channel as an outlet channel for the fluid flow. As a result of the connection via the exchangeable pneumatic module, a fluid flow from one of the channels enters the other channel. The exchangeable pneumatic module acts on the fluid flow in a fluid-mechanical manner, for example, in the manner of a throttle, i.e., by bringing about a pressure drop. The exchangeable pneumatic module is inventively configured as a pneumatic module in accordance with the disclosed embodiments. The pneumatic module can therefore be assembled and exchanged easily. For example, the support sleeve can be at least sectionally angular in configuration, allowing it to be screwed in or removed using a tool such as a socket wrench. Alternatively or additionally, a face at a free end of the pneumatic module can have a recess for inserting a tool, for example, an internal hexagonal hole. The gas analysis device can also have a heating element and/or a cooling element that is arranged adjacent to the pneumatic module. An adjacent arrangement is understood to mean that heat emitted from the heating element or absorbed by the cooling element acts on the pneumatic module in a way that can be detected. The inventive pneumatic module offers adequate thermal shielding for the flow module that is arranged therein, and therefore greater measuring accuracy can still be achieved using the gas analysis device despite the positioning of the pneumatic module adjacent to the heating element or cooling element. The gas analysis device can be configured as a gas analyzer or as a gas chromatograph. Thus the analysis that can be achieved using the gas analysis device is increased via the inventive pneumatic module. The pneumatic module can also be exchanged quickly and easily. In connection with the conduction block in particular, the gas analysis device allows particularly resilient operation and greater ease of repair.

The objects and advantages in accordance with the invention are likewise achieved by an inventive computer program product that is analysis to simulate the operating characteristics of a pneumatic module in a gas analysis device. The pneumatic module is inventively analysis in accordance with the disclosed embodiments.

For the purpose of simulation, the computer program product can have a physics module in which the pneumatic module is at least partially represented. In order to achieve this, for example, the pneumatic module can be replicated in its structure and functioning, for example, in the form of a digital representation that is part of the computer program product. Alternatively or additionally, the pneumatic module can also take the form of a mathematical model in the physics module. The physics module is designed inter alia to portray the thermal or aerodynamic characteristics of the pneumatic module under operating conditions that can be adjusted. The operating conditions that can be adjusted include, for example, an ambient temperature, a temperature of the fluid that is fed in, a thermal conductivity of the fluid and/or wall of the flow module, a heat conducting characteristic in the support sleeve, a feed pressure, an inflow speed, and/or a viscosity of the fluid. The computer program product can have a data interface via which corresponding data can be preset via a user input, a data connection to a real pneumatic module or gas analysis device and/or other simulation-related computer programs. The computer program product can also have a data interface for outputting simulation results to a user and/or other simulation-related computer program products. It is possible via the computer program product to detect, for example, a defective flow module, a faulty connection between the support sleeve and the flow module and/or a leak at a feed channel and/or outlet channel of the pneumatic module. In particular, the operating characteristics of the pneumatic module, expressed in the form of measured values in channels of a conduction block of the gas analysis device, can be checked for plausibility via correlation with the simulated pneumatic module. In addition, the pneumatic module can easily be modeled, i.e., recalculated with a minimum of CFD calculations in the operating characteristics. In particular, the flow characteristics in the flow module can be approximated with sufficient precision via algebraic calculation. The inventive computer program product therefore allows the pneumatic module concerned to be modeled with a reduced requirement for computing power. This means that a multiplicity of such pneumatic modules can be replicated, e.g., in a monitoring unit of the gas analysis device. It is thus easily possible to provide a particularly realistic process image of the operation of the gas analysis device. The computer program product can be designed as a so-called digital twin, as described in the U.S. Pub. No. 2017/286572 A1, for example. The disclosure of U.S. Pub. No. 2017/286572 A1 is included in the present application by virtue of reference thereto, i.e., is incorporate by reference herein in its entirety. The computer program product can be of monolithic design, i.e., executable in its entirety on a single hardware platform. Alternatively, the computer program product can be modular in design and comprise a plurality of subprograms that are executable on separate hardware platforms and interact via a communicative data connection. Such a communicative data connection can be a network connection, an internet connection and/or a mobile radio connection. The inventive computer program product can also test and/or optimize a pneumatic module via simulation.

The objects and advantages in accordance with the invention are likewise achieved by an inventive monitoring method for a pneumatic module. The monitoring method is used to monitor the operation of a pneumatic module that is deployed in a gas analysis device. The monitoring method comprises a first step, in which the pneumatic module is provided in an active operating state in the gas analysis device. Also provided in the first step is at least one measured value that is obtained following a fluid-mechanical influence of the pneumatic module on a fluid flow in the gas analysis device. Also detected and provided is at least one operating variable via which the current operating state of the gas analysis device is specified. The method further comprises a second step, in which the at least one operating variable is provided to a computer program product as an input. Based on the operating variable provided, a reference measured value is determined by the computer program product in the second step, where the reference measured value corresponds to the measured value provided in the first step. The method comprises a third step, in which the reference measured value and the measured value are compared with each other. If a difference between the measured value and the reference measured value exceeds the amount of an adjustable threshold value, then a warning is output to a user and/or a control unit of the gas analysis device. It is additionally possible in a fourth step, based on the reference measured value and the measured value, via a recognition algorithm to identify a cause for the difference between the measured value and the reference measured value. The recognition algorithm can be formed as a neural network, for example. The computer program product deployed in the second step is inventively configured in accordance with the disclosed embodiments.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention is explained in greater detail below with reference to individual embodiments in figures. The figures are to be considered mutually complementary in that identical reference signs have the same technical significance in different figures. The features of the individual embodiment can also be combined with each other. Furthermore, the embodiments shown in the figures can be combined with the features outlined above, in which.

DETAILED DESCRIPTION OF THE EXEMPLARY EMBODIMENTS

Figure 1:
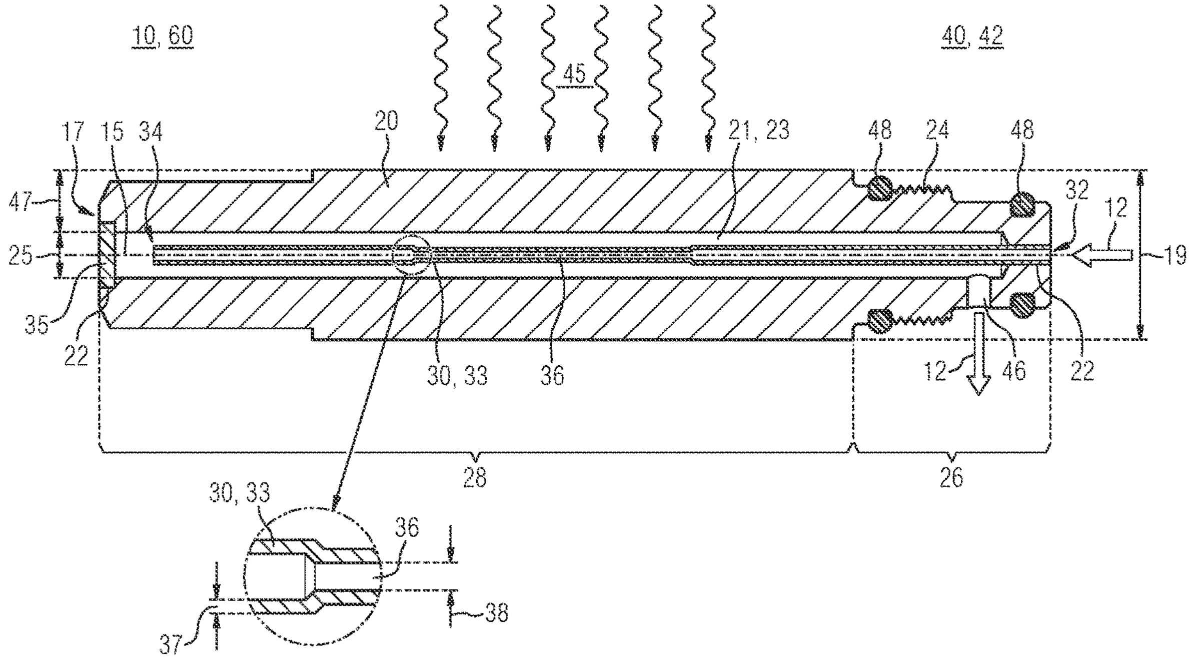
FIG. 1 shows a longitudinal section of a first embodiment of the pneumatic module in accordance with the invention.

FIG. 1 illustrates a structure of a first embodiment of the inventive pneumatic module 10 in a longitudinal section. The pneumatic module 10 comprises a support sleeve 20 with an interior chamber 21 that is formed therein and in which a flow module 30 is arranged along a main axis 15 of the support sleeve 20. The support sleeve 20 itself is formed as a single part. The flow module 30 is configured as a pinch throttle 33 and has a constriction 36 in a central region. The flow module 30 is connected in the region of a first end 32 to the support sleeve 20 via a non-detachable connection 22 that is formed as a connection with a material bond. The first end 32 of the flow module 30 is arranged in a first section 26 of the support sleeve 20 such that a fluid flow 12 can enter in an assembled state of the pneumatic module 10. The fluid flow 12 flows through the flow module 30 and emerges into the interior chamber 21 of the support sleeve 20 at a second end 34 of the flow module 30. As a result of the flow module 30, the interior chamber 21 of the support sleeve 20 at least sectionally takes the form of a circumferential thin intermediate space 23. An outlet opening 48 is formed in the first section 26 of the support sleeve 20 and extends in an essentially radial direction relative to the main axis 15. The fluid flow 12 emerges via the outlet opening 46 in an active operating state of the pneumatic module 10. Furthermore, in the first section 26 of the support sleeve 20, a thread 24 is formed on an exterior surface of the support sleeve 20 and allows the pneumatic module 10 to be assembled into a conduction block 42 (not shown) of a gas analysis device 40. Furthermore, a sealing structure 48 is arranged in the first section 26 of the support sleeve 20. In the region of the second end 34 of the flow module 30, a cover 35 is arranged at a free end 17 of the support sleeve 20 and therefore of the pneumatic module 10. The cover 35 is likewise connected to the support sleeve 20 with a non-detachable connection 22. The support sleeve 20 is configured to be closed by the cover 35.

The support sleeve 20 ensures that the flow module 30 is shielded mechanically against the environment. The flow module 30 is likewise shielded against any heat input 45 from the environment. In order to ensure the mechanical and thermal shielding of the flow module 30, the support sleeve 20 has a sufficient sleeve wall thickness 47 and the flow module 30 has a wall thickness 37. The support sleeve also has a maximum outer diameter 19. This ensures adequate mechanical stability of the support sleeve 20, which also allows safe handling of the pneumatic module 10 but is compact at the same time. Accordingly, the flow module 30 is delicately formed and has a wall thickness 37 of up to 5 mm and/or a minimum inner diameter 38 of 1 μm to 2.0 mm. Furthermore, the non-detachable connection 22 between the support sleeve 20 and the flow module 30 is compact in structure. The support sleeve 20 therefore acts partially as a heat sink and the effect on the flow module 30 of a heat input 45 from the environment is reduced.

Both the support sleeve 20 and the flow module 30 are produced from a metallic material. The respective materials are selected so as to form an advantageous material pairing with respect to weldability. The non-detachable connection 22 is produced automatically via laser welding. Heat input into the flow module 30 is minimized and distortion of the flow module 30 is prevented thereby during the production of the pneumatic module 10. The pneumatic module 10 can therefore be produced precisely with increased process reliability. The pneumatic module 10 is represented by a computer program product 60 that is formed as a so-called digital twin. The computer program product 60 is configured to simulate the operating characteristics of the pneumatic module 10. In particular, it is possible thereby to simulate the characteristics of the fluid flow 12 as it flows through the pneumatic module 10.

Figure 2:
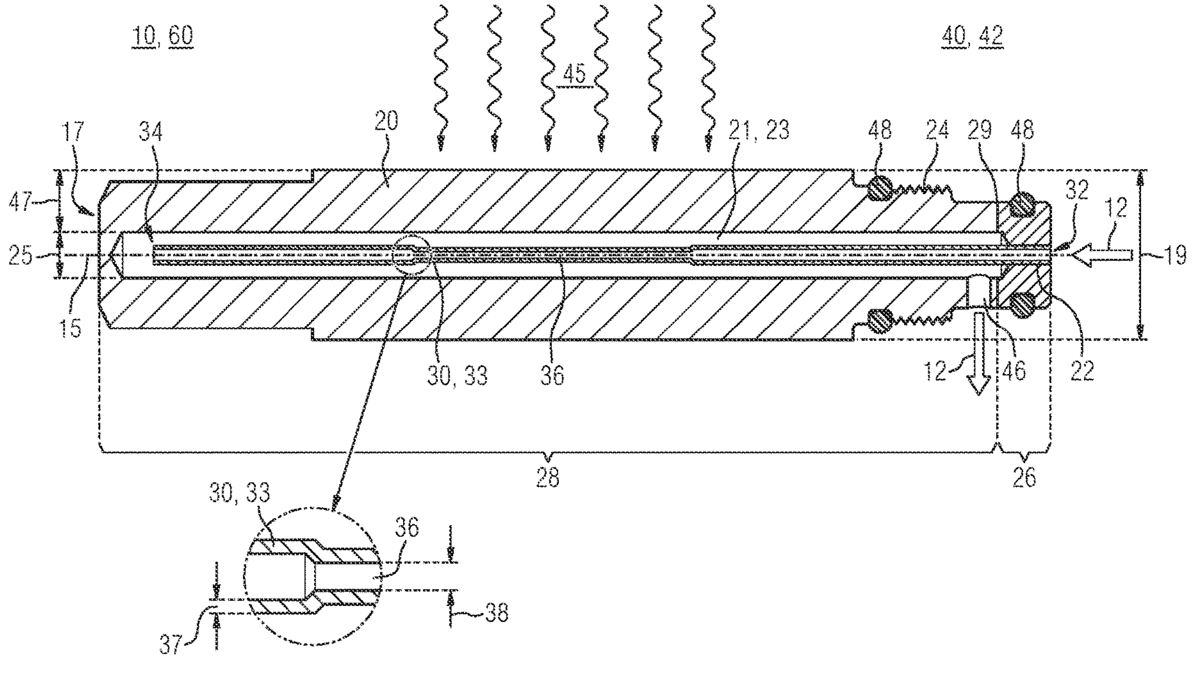
FIG. 2 shows a longitudinal section of a second embodiment of the pneumatic module in accordance with the invention.

A second embodiment of the inventive pneumatic module 10 is illustrated in FIG. 2 in a longitudinal section parallel to the main axis 15 thereof. The pneumatic module 10 comprises a support sleeve 20 with an interior chamber 21 which is formed therein and in which a flow module 30 is arranged along a main axis 15 of the support sleeve 20. The support sleeve 20 comprises a first section 26 and an adjoining second section 28. The first and second sections 26, 28 are connected together at a joining point 29 and are produced from respectively different metallic materials. The joining point 29 takes the form of a connection with a material bond. The flow module 30 is formed as a pinch throttle 33 and has a constriction 36 in a central region. The flow module 30 is connected in the region of a first end 32 to the first section 26 of the support sleeve 20 via a non-detachable connection 22 which takes the form of a connection with a material bond. The first end 32 of the flow module 30 is arranged in the first section 26 of the support sleeve 20 such that a fluid flow 12 can enter in an assembled state of the pneumatic module 10. The flow module 30 can be connected to the first section 26 of the support sleeve 28 during production. The second section 28 of the support sleeve 30 can then be connected to the first section 26. The handling of the flow module 30 during production is thereby further simplified.

The fluid flow 12 flows through the flow module 30 and emerges into the interior chamber 21 of the support sleeve 20 at a second end 34 of the flow module 30. As a result of the flow module 30, the interior chamber 21 of the support sleeve 20 at least sectionally takes the form of a circumferential thin intermediate space 23. An outlet opening 48 is formed in the first section 26 of the support sleeve 20 and extends in an essentially radial direction relative to the main axis 15. The fluid flow 12 emerges via the outlet opening 46 in an active operating state of the pneumatic module 10. Furthermore, in the first section 26 of the support sleeve 20, a thread 24 is formed on an exterior surface of the support sleeve 20 and allows the pneumatic module 10 to be assembled into a conduction block 42 (not shown) of a gas analysis device 40. Furthermore, a sealing structure 48 is arranged in the first section 26 of the support sleeve 20. In the region of the second end 34 of the flow module 30, the support sleeve 20 is configured to be closed at a free end 17. In contrast with the first embodiment shown in FIG. 1, the cover 35 thereof is omitted in the embodiment of FIG. 2.

The support sleeve 20 ensures that the flow module 30 is shielded mechanically against the environment. The flow module 30 is likewise shielded against any heat input 45 from the environment. In order to ensure the mechanical and thermal shielding of the flow module 30, the support sleeve 20 has a sufficient sleeve wall thickness 47 in its second section 28. The support sleeve also has a maximum outer diameter 19 in its second section 28. This ensures adequate mechanical stability of the support sleeve 20, which also allows safe handling of the pneumatic module 10 but is compact at the same time. Accordingly, the flow module 30 is delicately formed and has a wall thickness 37 of up to 5 mm and/or a minimum inner diameter 38 of 1 μm to 2.0 mm. Furthermore, the non-detachable connection 22 between the support sleeve 20 and the flow module 30 is compact in structure. The support sleeve 20 therefore acts partially as a heat sink and the effect on the flow module 30 of a heat input 45 from the environment is reduced.

Both the support sleeve 20 and the flow module 30 are produced from a metallic material. The respective materials are selected so as to form an advantageous material pairing with respect to weldability. The non-detachable connection 22 is produced automatically via laser welding. Heat input into the flow module 30 is minimized and distortion of the flow module 30 is prevented thereby during the production of the pneumatic module 10. The pneumatic module 10 can therefore be produced precisely with increased process reliability. The pneumatic module 10 is represented by a computer program product 60 that is configured as a so-called digital twin. The computer program product 60 is configured to simulate the operating characteristics of the pneumatic module 10. In particular, it is possible thereby to simulate the characteristics of the fluid flow 12 as it flows through the pneumatic module 10.

Figure 3:
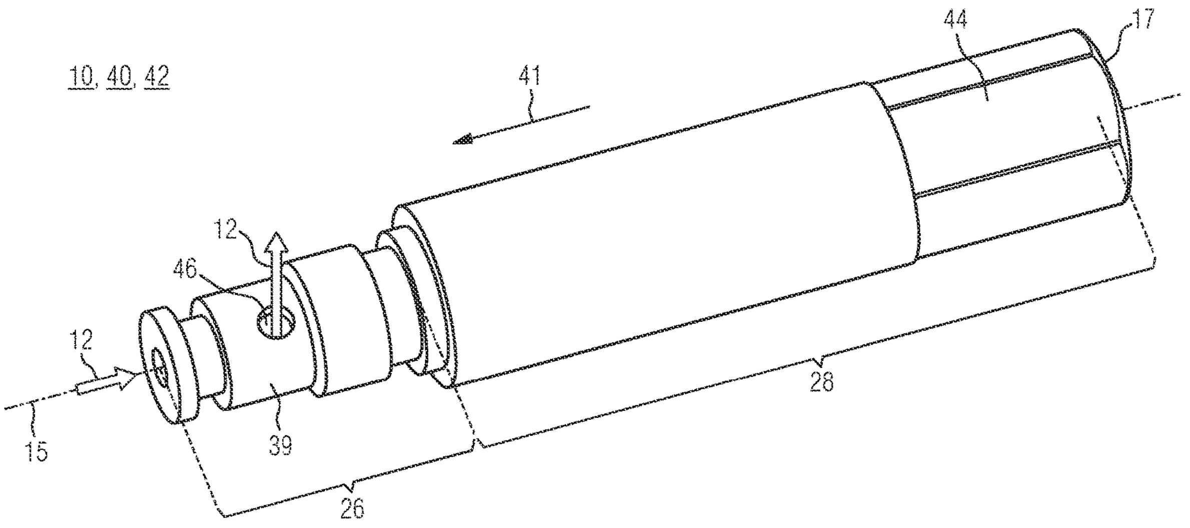
FIG. 3 shows an oblique view of a third embodiment of the pneumatic module in accordance with the invention.

A third embodiment of the inventive pneumatic module 10 is illustrated in an oblique view in FIG. 3. The pneumatic module 10 comprises a support sleeve 20, which extends essentially along a main axis 15. The support sleeve 10 has a first section 26, which is configured to introduce a fluid flow 12 into the pneumatic module 10. The first section 26 is provided with retaining projections and shoulders, which allow assembly into a conduction block 42 (not shown) of a gas analysis device 40. For the purpose of fixing the pneumatic module 10 in the gas analysis device 40, it is inserted into the conduction block 42 in an assembly direction 41. With the retaining projections and shoulders, the first section 26 of the support sleeve 20 is configured as a compressed-air connection interface 39. An outlet opening 46 through which a fluid flow 12 emerges during operation of the pneumatic module 10 is also formed in the first section 26. In a second section 28 of the support sleeve 20, which adjoins the first section 26, a tool extension 44 is formed in the region of a free end 17. The tool extension 44 is angular, in particular having six sides, so that the pneumatic module 10 can be gripped by a tool at the tool extension 44 for the purpose of assembly or disassembly. A flow module 30 (not shown) through which the incoming fluid flow 12 flows is contained in the support sleeve 20. In contrast with the fluid flow 12 entering, the fluid flow 12 emerging from the outlet opening 46 exhibits a total pressure drop. The interior of the pneumatic module 10 can be configured as per FIG. 1 or FIG. 2. The pneumatic module 10 can likewise be simulated in its operating characteristics by a computer program product 60 (not shown). The computer program product 60 is formed as a so-called digital twin.

Figure 4:
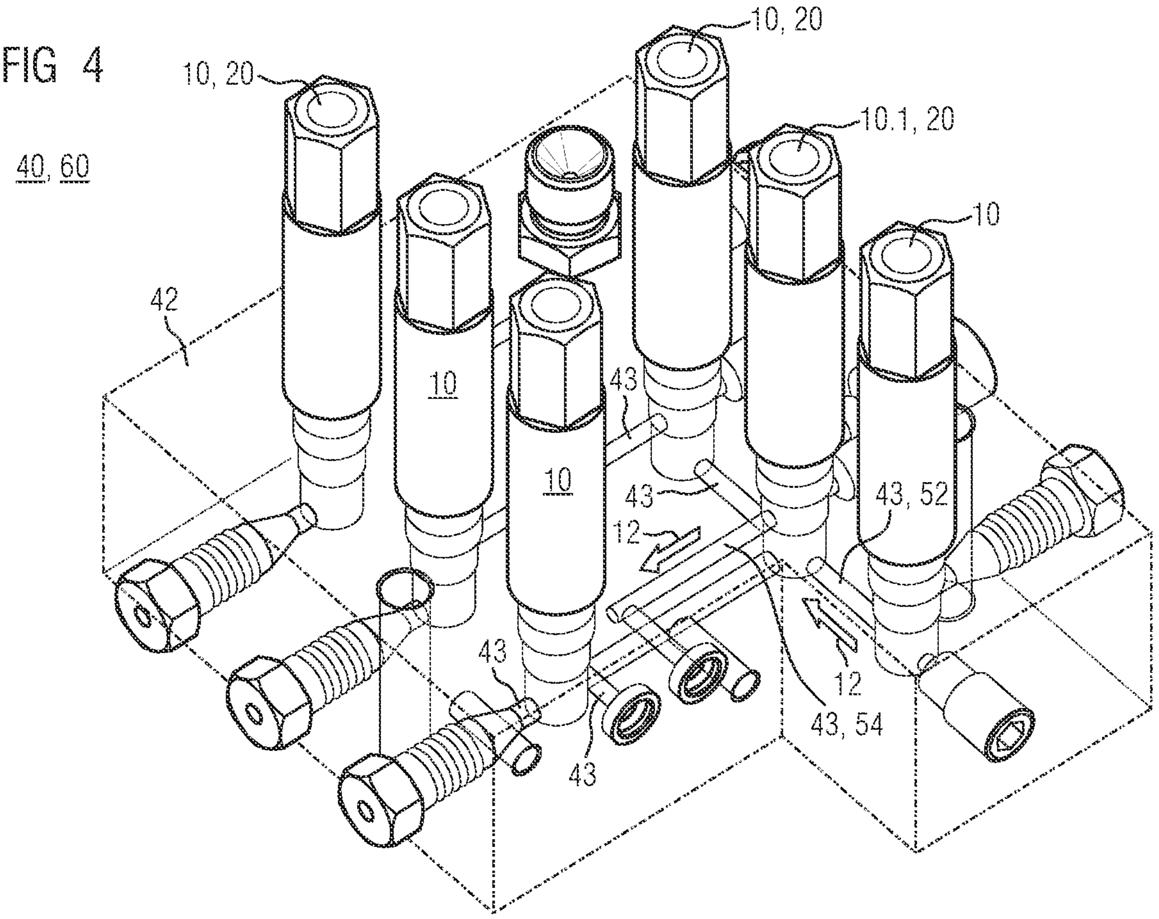
FIG. 4 shows a partially transparent oblique view of an embodiment of part of a gas analysis device in accordance with the invention.

FIG. 4 schematically shows part of an embodiment of an inventive gas analysis device 40. The gas analysis device 40 comprises a conduction block 42 in which a plurality of channels 43 are formed. The channels 42 are voids within the conduction block 42. For greater clarity, the conduction block 42 is illustrated in a transparent manner in FIG. 3. In addition to this, a plurality of pneumatic modules 10 are detachably held in the conduction block 42, i.e., they can be non-destructively detached therefrom. A first pneumatic module 10.1 is connected to a channel 43 which is formed as a feed channel 52 and through which a fluid flow 12 is guided into the first pneumatic module 10.1. After flowing through the first pneumatic module 10.1, the fluid flow 12 emerges via a channel 43 that serves as an outlet channel 54. The feed channel 52 is connected to the outlet channel 54 via the first pneumatic module 10.1 accordingly. The channels 43 are similarly connected via the further pneumatic modules 10. By virtue of the channels 43 being formed as voids in the conduction block 42, they are resilient against influences from the environment, in particular mechanical influences. The pneumatic modules 10, 10.1 are similarly resilient against mechanical and thermal influences from the environment. The pneumatic modules 10, 10.1 can be formed in accordance with the embodiments shown in FIG. 1, FIG. 2 or FIG. 3 and have correspondingly reduced dimensions.

The channels 43 have diameters that are adapted to the dimensions of the pneumatic modules 10, 10.1. The conduction block 42 is correspondingly compact in structure. This allows greater miniaturization of the associated gas analysis device 40 at the same time as increased resilience. Furthermore, the pneumatic modules 10, 10.1 have support sleeves 20 that are formed as identical parts. The pneumatic modules 10, 10.1 can therefore be mutually exchanged. The pneumatic modules 10 can be exchanged easily, and therefore repair of the gas analysis device 40 is accelerated. Furthermore, the conduction block 42 can be deployed as an identical part for different structural types of gas analysis device 40. The conduction block 42 can be adjusted with respect to its fluid-mechanical characteristics by providing different pneumatic modules 10, 10.1, the pneumatic modules 10, 10.2 differing by virtue of their respective flow modules 30. That part of the gas analysis device 40 shown in FIG. 5 therefore realizes a modular concept for different structural types of gas analysis device 40. Furthermore, the operating characteristics of at least one pneumatic module 10, 10.1 can be simulated during operation of the gas analysis device 40 via a computer program product 60 that is formed as a digital twin of the respective pneumatic module 10, 10.1.

Figure 5:
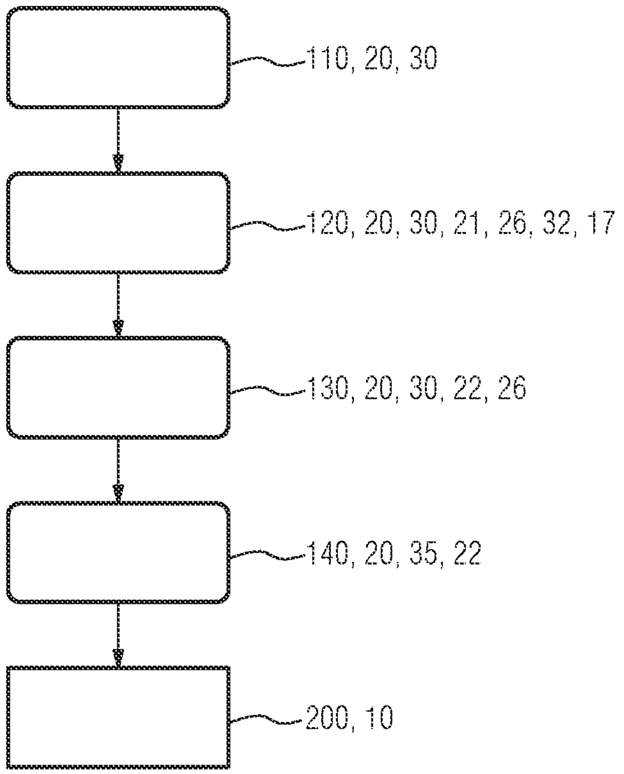
FIG. 5 schematically shows a sequence of an embodiment of the method in accordance with the invention.

A sequence of an embodiment of the inventive method 100 is shown schematically in FIG. 5. The method 100 relates to the production of a pneumatic module 10 which is configured for use in a gas analysis device 40 (not shown). The method 100 comprises a first step 110, in which a support sleeve 20 and a flow module 30 are provided for use as workpieces for the pneumatic module 10. In a second step 120 following thereupon, the flow module 30 is inserted into an interior chamber 21 of the support sleeve 20. The insertion is made through an opening at a free end 17 of the support sleeve 20. In the region of a first end 32, the flow module 30 fits tightly in a first section 26 of the support sleeve 20 and is oriented so as to guide a fluid flow 12 into the interior chamber 21 of the support sleeve 20. The first section 26 of the support sleeve 20 is situated at an opposite end of the support sleeve 20 to the free end 17. Thus the flow module 20 reaches a designated assembly position in the second step 120. The second step 120 is performed automatically, in particular via a robot.

The method 100 further comprises a third step 130 that follows thereupon and in which a non-detachable connection 22 is produced between the support sleeve 20 and the flow module 30. The non-detachable connection 22 is formed as a connection with a material bond and cannot be detached without destruction. The non-detachable connection 22 is formed in the region of the first end 32 of the flow module 30. The third step 130 is likewise performed automatically, in particular via a robot. The third step 130 is followed by a fourth step 140, in which a cover 35 is provided and positioned at the free end 17 of the support sleeve 20. The opening at the free end 17 of the support sleeve 20 is closed by the cover 35. A non-detachable connection 22 between the cover 35 and the support sleeve 20 is also produced in the fourth step 140. Following the fourth step 140, the method 100 reaches an end state 200 in which the pneumatic module 10, having been produced in this way, is available. The pneumatic module 10 that has been produced via the method 100 is represented in a computer program product 60 (not shown) which is suitable for simulating the operating characteristics thereof.

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A pneumatic module for adjusting a fluid flow in a gas analysis device, comprising:

a support sleeve comprising a first section, a thread being formed in an exterior surface of the support sleeve, and the thread being configured to allow assembly of the pneumatic module into a conduction block in the gas analysis device; and a flow module which is contained in the support sleeve;

wherein the flow module is connected at a first end thereof to the support sleeve to achieve greater accuracy of measurements performed by the gas analysis device.

2. The pneumatic module as claimed in claim 1, wherein the flow module is connected in one of a non-detachable manner and detachable manner to the support sleeve in the region of a first end of the flow module.

3. The pneumatic module as claimed in claim 1, wherein a second end of the flow module opens into an interior chamber of the support sleeve.

4. The pneumatic module as claimed in claim 2, wherein a second end of the flow module opens into an interior chamber of the support sleeve.

5. The pneumatic module as claimed in claim 1, wherein the support sleeve is configured, in the region of the first end of the flow module, for assembly into the gas analysis device.

6. The pneumatic module as claimed in claim 2, wherein the support sleeve is configured, in the region of the first end of the flow module, for assembly into the gas analysis device.

7. The pneumatic module as claimed in claim 3, wherein the support sleeve is configured, in the region of the first end of the flow module, for assembly into the gas analysis device.

8. The pneumatic module as claimed in claim 1, wherein the support sleeve is formed as a single part or from multiple parts.

9. The pneumatic module as claimed in claim 1, wherein the support sleeve is configured to be closed in a region of a second end of the flow module.

10. The pneumatic module as claimed in claim 9, wherein the support sleeve is configured to be closed by a cover fixed in a non-detachable manner in the region of the second end of the flow module.

11. The pneumatic module as claimed in claim 1, wherein at least one of (i) the flow module and (ii) the support sleeve is produced at least partially from a metallic material.

12. The pneumatic module as claimed in claim 1, wherein the flow module has at least one of (i) a minimum inner diameter of 1 μm to 2.0 mm and (ii) a wall thickness of up to 5.0 mm.

13. The pneumatic module as claimed in claim 1, wherein the flow module is formed as a pinch throttle.

14. A gas analysis device comprising:

a conduction block having a plurality of channels;

wherein at least two channels are connected together via an exchangeable pneumatic module for adjusting a fluid flow in the gas analysis device and having a first portion which is accommodated in the conduction block;

wherein the pneumatic module comprises a support sleeve comprising a first section, a thread being formed in an exterior surface of the support sleeve, and the thread being configured to allow assembly of the pneumatic module into a conduction block in the gas analysis device, and the pneumatic module further comprises a flow module which is contained in the support sleeve; and wherein the flow module is connected at a first end thereof to the support sleeve to achieve greater accuracy of measurements performed by the gas analysis device.

15. A non-transitory computer-readable medium storing program instructions which, when executed by at least one processor, cause simulation of operational characteristics of a pneumatic module utilized in a gas analysis device into which a fluid flow is fed; wherein the program instructions cause the simulation to utilize a representation of the pneumatic module; wherein the pneumatic module comprises a support sleeve including a first section, a thread being formed in an exterior surface of the support sleeve, and the thread being configured to allow assembly of the pneumatic module into a conduction block in the gas analysis device and including a flow module which is contained in the support sleeve; and wherein the flow module is connected at a first end thereof to the support sleeve such that greater accuracy of measurements performed by the gas analysis device is achievable.

* * * * *